United States Patent
Fernie

[11] Patent Number: 5,972,126
[45] Date of Patent: Oct. 26, 1999

[54] SELF-CLEANING HAND WASHER

[75] Inventor: Geoffrey Roy Fernie, Etobicoke, Canada

[73] Assignee: Sunnybrook & Women's College Health Sciences Centre, North York, Canada

[21] Appl. No.: 09/188,351

[22] Filed: Nov. 10, 1998

Related U.S. Application Data

[63] Continuation-in-part of application No. 08/692,226, Aug. 7, 1996, Pat. No. 5,860,437.

[51] Int. Cl.$^6$ .................................................... B08B 3/02
[52] U.S. Cl. ................................. 134/18; 134/26; 134/29; 134/42; 134/95.2; 134/95.3; 134/104.1; 134/57 R
[58] Field of Search ................................. 134/18, 26, 42, 134/29, 95.2, 95.3, 104.1, 57 R

[56] References Cited

U.S. PATENT DOCUMENTS

| | | | |
|---|---|---|---|
| 2,641,771 | 6/1953 | Schiro | 4/182 |
| 3,699,984 | 10/1972 | Davis | 134/95 |
| 3,918,987 | 11/1975 | Kopfer | 134/95 |
| 4,219,367 | 8/1980 | Cary | 134/29 |
| 4,817,651 | 4/1989 | Crisp | 134/102 |
| 5,193,563 | 3/1993 | Melech | 134/100.1 |
| 5,199,118 | 4/1993 | Cole et al. | 4/619 |
| 5,265,628 | 11/1993 | Sage et al. | 134/58 R |
| 5,727,579 | 3/1998 | Chardack | 134/95.2 |

FOREIGN PATENT DOCUMENTS

9-279659  10/1997  Japan .

*Primary Examiner*—Zeinab El-Arini
*Attorney, Agent, or Firm*—Philip C. Mendes da Costa; Bereskin & Parr

[57] ABSTRACT

A method for a person to wash their hands using a hand washing apparatus comprising a hand washing bowl having an interior and a cover which are reconfigurable between a hand washing position in which the person can wash their hands and an inactive position, a controller for reconfigurating the bowl between the hand washing position and the inactive position; and, a dispenser for dispensing water and a cleaner over the person's hands, the method comprising the steps of actuating the controller to rotate the bowl and the cover about an axis to the hand washing position; dispensing water and soap over the person's hands; and, dispensing water to rinse the person's hands.

17 Claims, 6 Drawing Sheets

SELF-CLEANING HAND WASHER

This application is a constitution-in-part application of U.S. patent application Ser. No. 08/692,226 filed on Aug. 7, 1996, now U.S. Pat. No. 5,860,437.

FIELD OF THE INVENTION

The invention relates to hand washing machines and, in particular, to a method of using a self-contained hand washing machine which may be self-cleaning between each usage.

BACKGROUND OF THE INVENTION

Washing of the hands is believed to be one of the first safeguards against spreading infection, whether in a health care institution, or in any other facility or location. However, the facilities which are usually provided for hand washing are to say the least somewhat primitive, and have scarcely changed in design since plumbing was first introduced. Most hand washing facilities are based on a basin, with hot and cold water taps, and a source of soap. Drying of the hands is at best dependent on disposable paper towels, or in many cases by hot air hand dryers.

Disposable paper towels frequently do not get rid of all of the residue from washing. Disposal of the towels may result in recontamination of the hands. Hot air drying of the hands uses small appliances with fans and electrical heating coils. These appliance when brand new work reasonably well, simply blowing fresh air over the hands. However, after even a small amount of usage contaminated air is drawn into the hand dryer and bacteria may accumulate in the warm, moist atmosphere of the dryer. The result is that from then on the hands are dried in air which may be carrying a substantial volume of bacteria.

Even the multiple washing of the hands many times does not overcome these problems.

A further problem is that the sink or basin in which the washing water is collected itself becomes a source of contamination after only a very few usages. Dirt and dried soap collect, and breed bacteria in the basin itself.

The operation of the handles on the faucets is itself yet another source of contamination. Persons may turn the faucets on and off, for example, after relieving themselves, when their hands are actually contaminated, and thereby leaving contamination on the handles of the faucets. For all of these reasons, therefore, the use of conventional hand washing facilities, even those in health care institutions, is unsatisfactory and unhygienic and may actually result in the spreading of infection and bacteria, rather than the reverse.

BRIEF SUMMARY OF THE INVENTION

According to the instant invention, there is provided a hand washing apparatus comprising a hand washing bowl and a cover, the bowl and cover being reconfigurable between a hand washing position and an inactive position in which the bowl is closed by the cover; a controller for reconfigurating the bowl between the hand washing position and the inactive position; and, a dispenser for dispensing water, a cleaner and rinse water over hands in the bowl.

In an alternate embodiment, the hand washing apparatus comprises a hand washing bowl mounted at a suitable height for washing hands; a controller for opening the bowl into a hand washing position and closing the bowl into an inactive position; a warm water dispenser for dispensing warm water over hands in the bowl; a soap dispenser for dispensing soap over hands in the bowl; and, a rinse water dispenser for dispensing rinse water over hands in the bowl.

In a further alternate embodiment, the hand washing apparatus comprises a hand washing bowl and a cover, the bowl and cover being reconfigurable between a hand washing position and an inactive position in which the bowl is closed by the cover; a dispenser for dispensing water, a cleaner and rinse water over hands in the bowl; and, a controller actuated without use of the hands of the user for actuating the reconfiguration of the bowl and the cover between the hand washing position and the inactive position.

The bowl may be mounted at a suitable height for washing hands and is mounted for rotation about a generally horizontal axis between the hand washing position and the inactive position. The bowl may be of a generally hemispherical shape and when the bowl is in the hand washing position, the bowl is open upwardly for access by a user and when in the inactive position, the interior of the bowl is inaccessible by a user.

The hand washing apparatus may include an air dryer for generating a stream of hot air flowing over the hands of a user, the air dryer being operable by the user without touching the apparatus. Preferably, the air dryer is automatically operable after completion of a washing cycle. The hot air may be disinfected prior to flowing over the hands of a user.

The hand washing apparatus may include a discharger for discharging a disinfectant into the bowl when the bowl is in its inactive position, for flowing around the interior of the bowl and rendering the same clean. Further, an air stream may be provided to dry the bowl after the bowl has been cleaned.

A collection sink may be positioned to receive the liquid contents of the bowl when the bowl is in the inactive position.

The hand washing apparatus may include a sensor for recognizing a particular user prior to the activation of a washing cycle. The apparatus may have a controller that is preprogrammed with at least two different washing cycles, the user selects the desired washing cycle, and the apparatus includes a recording media to record the cycle that was selected by the particular user.

The apparatus may have a controller that is preprogrammed with at least two different washing cycles and the user selects the desired washing cycle.

The hand washing apparatus may also have a sensor for recognizing a particular user prior to the activation of a washing cycle, wherein the recognition of a particular user actuates the controller.

The hand washing apparatus may also have a foot pedal to actuate the controller.

According to the instant invention, there is also provided a method for a person to wash their hands using a hand washing apparatus comprising a hand washing bowl and a cover which are reconfigurable between a hand washing position and an inactive position, a controller for reconfigurating the bowl between the hand washing position and the inactive position; and, a dispenser for dispensing water and a cleaner over the user's hands, the method comprising the steps of actuating the controller to move the bowl and the cover to the hand washing position; dispensing water and soap over the user's hands; and, dispensing water to rinse the user's hands.

The method may also include dispensing a stream of hot air over the hands of a user.

The method may also include dispensing a disinfectant into the bowl when the bowl is in its inactive position, for flowing around the interior of the bowl and rendering the same clean. Further, the method may include dispensing an air stream to dry the bowl after the bowl has been cleaned.

The apparatus may also have a controller that is preprogrammed with at least two different washing cycles and the method may include selecting the desired washing cycle whereupon the various fluids are thereafter automatically dispensed.

The apparatus may also have a sensor for recognizing a particular user and the method may further comprise the step of using a card to identify the user to the apparatus prior to the activation of a washing cycle. Further, the user may present an identity card to the sensor to activate the apparatus.

One advantage of the instant invention is that it provides a hand washing facility in which the hands of the user need not touch the basin, taps or soap dispenser. The water may be mixed to the correct temperature automatically so that the taps do not have be manually operated. Accordingly, the cycle of operations may be controlled by automatic controls and timers so that no input is required from the user.

A further advantage of the instant invention is that in the inactive position of the bowl, the bowl is inaccessible so as to avoid collection of contamination. Thus, the entire apparatus is self-contained within a closed housing for security and cleanliness and requiring only regular maintenance by qualified trained personnel.

Further, the soap or other cleaning or rinsing composition is preferably dispensed automatically so it does not accumulate or substantially accumulate as a residue, and the basin is preferably rinsed and dried after each use so that the bowl is cleaned after each use to prevent bacteria from growing therein.

In some cases, hand drying aids such as towels can be provided for use in conjunction with the warm air drier.

The entire washer may be of such a compact unitary design that it can be installed almost anywhere, not merely in bathrooms. In this way, more frequent washing of the hands is encouraged, and the unit will maintain a clean, attractive appearance without daily maintenance.

BRIEF DESCRIPTION OF THE DRAWINGS

The various features of novelty which characterize the invention are pointed out with more particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention in which:

DESCRIPTION OF THE PREFERRED EMBODIMENT

Figure 1:
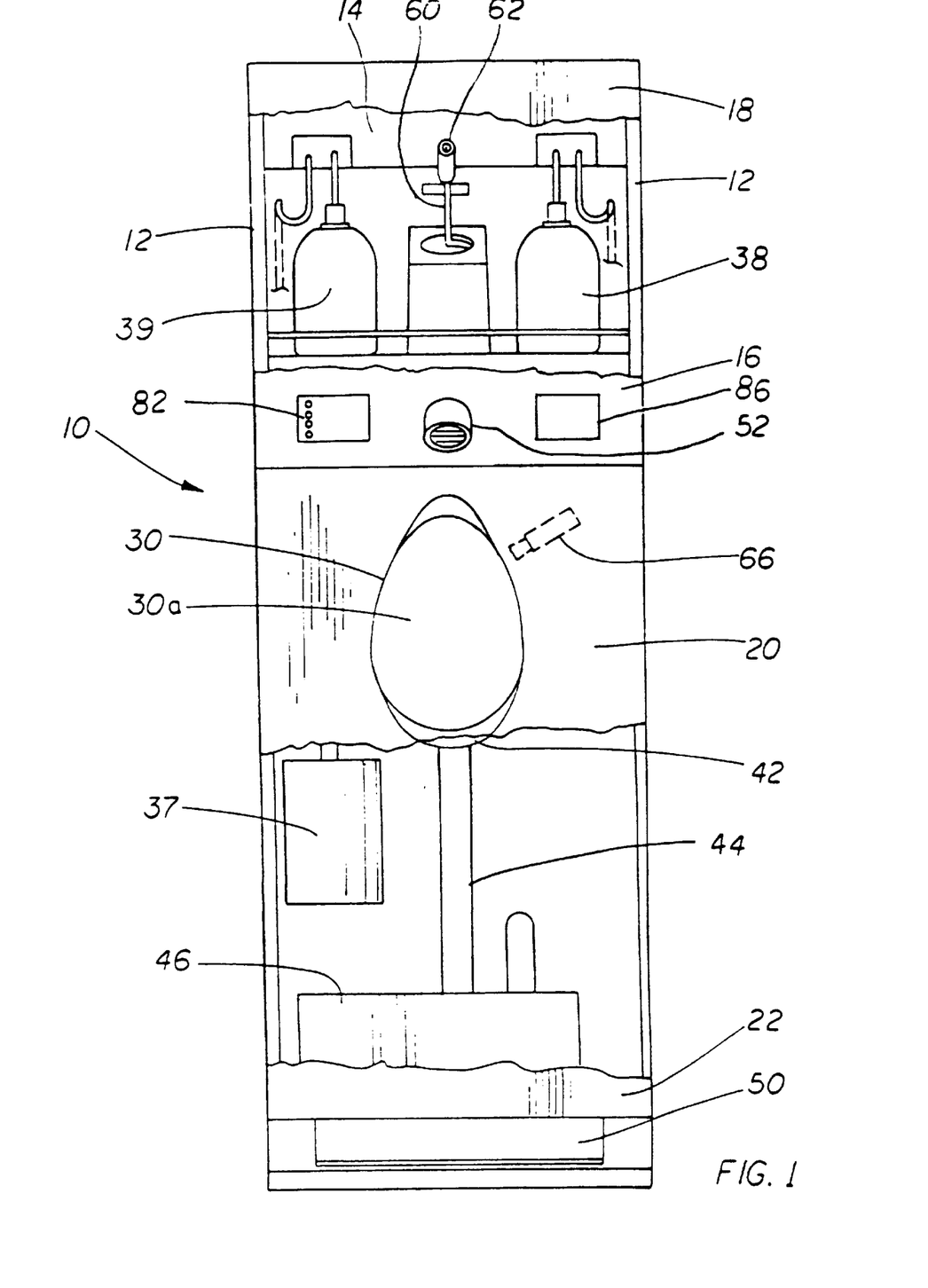
FIG. 1 is a front elevational view of the hand washing machine in accordance with a preferred embodiment of the invention, with the front removed so as to show various parts of the interior.
Figure 2:
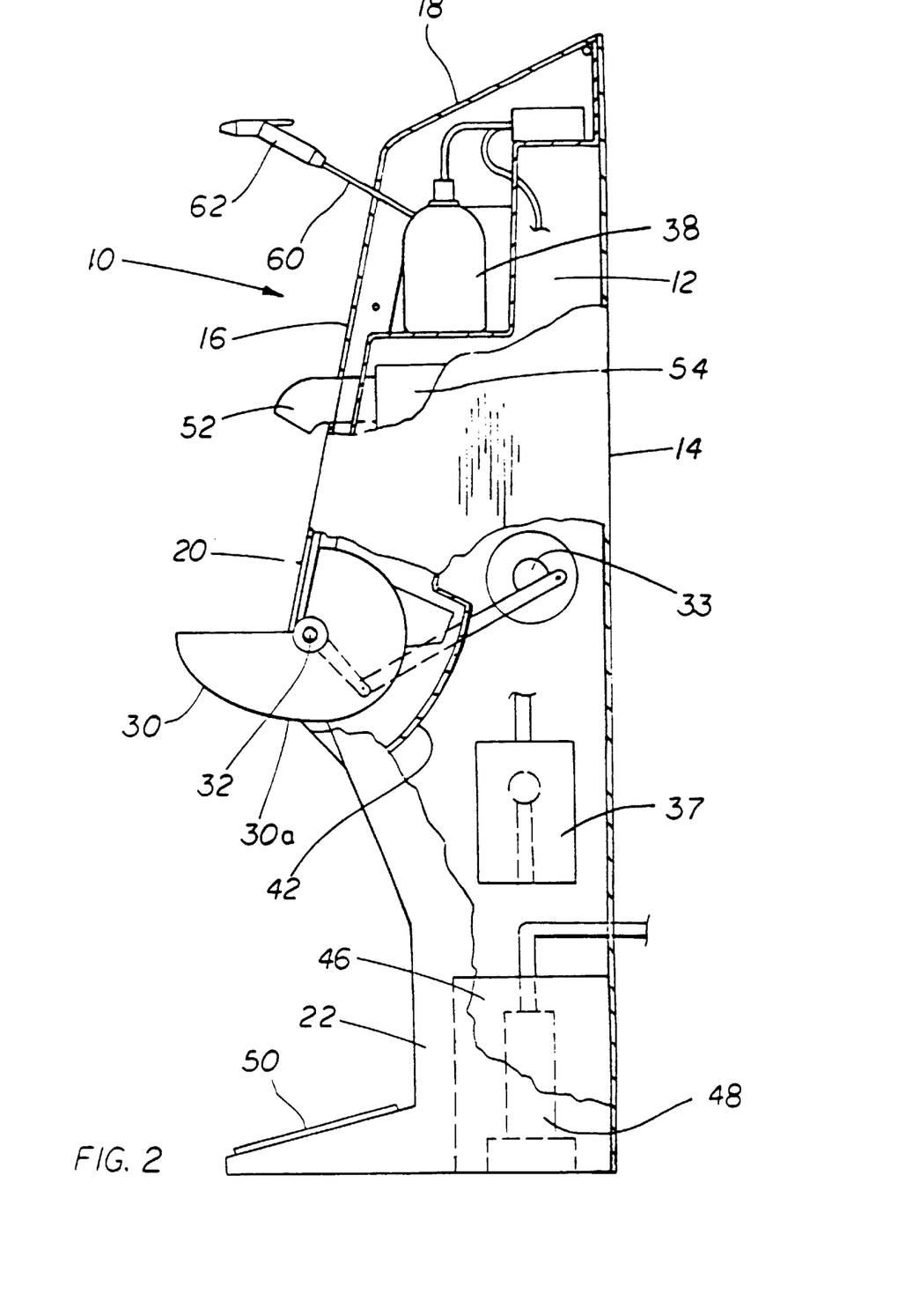
FIG. 2 is a side elevational view partly in section showing the machine in the hand washing position.

FIGS. 1 and 2 illustrate a hand washer demonstrating the various features of the invention, and comprising a generally rectangular upright housing 10 having sidewalls 12, 12 and a back wall 14. A contoured front wall 16 defines a roof 18, and forwardly projecting washing region 20. A recessed foot region 22 is defined at the lower end of front wall 16.

Within the front wall 16, on suitable framework, the details of which are omitted for the sake of clarity, there is a hand washing bowl indicated generally as 30. Bowl 30 is reconfigurable between an open configuration in which the bowl is configured for a user to wash their hands and a closed configuration in which bowl 30 may be cleaned after use. Preferably, bowl 30 is moveable between an open position in which the bowl is positioned for a user to wash their hands and a closed position in which bowl 30 may be cleaned after use. Alternately, the bowl 30 could be stationary and have a cover which moves to cover or uncover the bowl.

Figure 3:
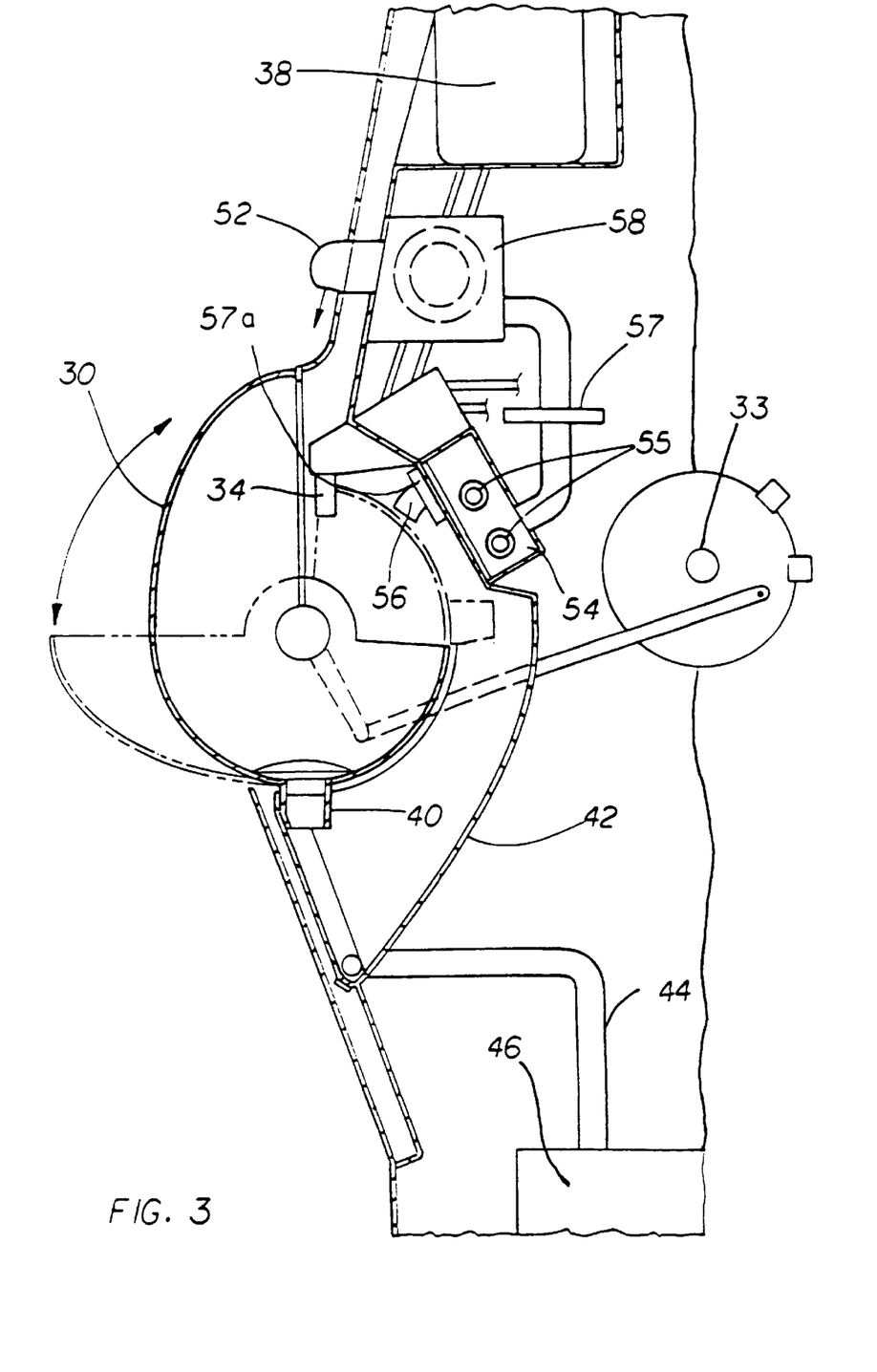
FIG. 3 is an enlarged sectional view corresponding to FIG. 2 showing the basin portion rotated inwardly for rinsing and disinfection.
Figure 4:
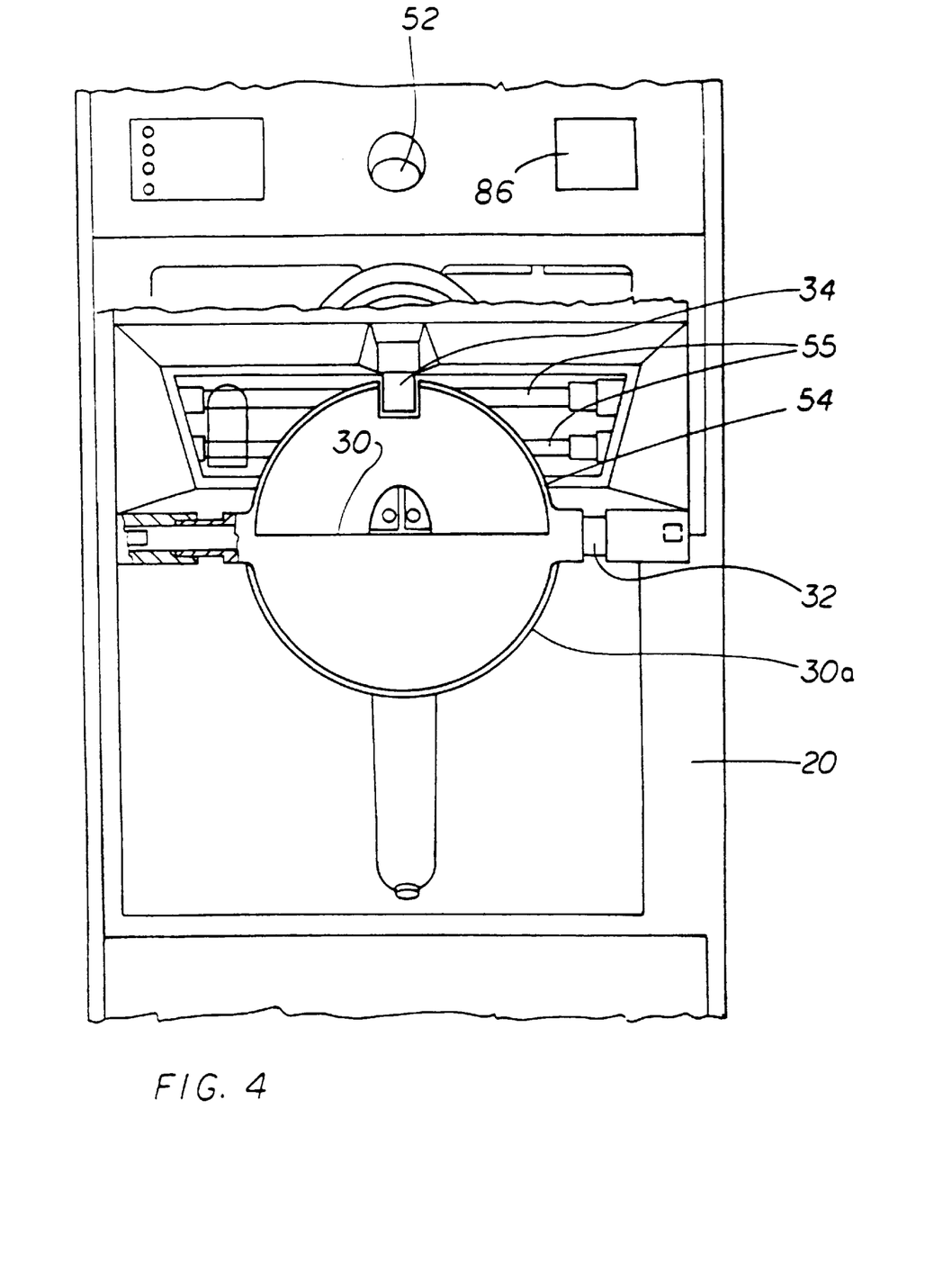
FIG. 4 is an enlarged front elevation view of the bowl with the bowl rotated to its hand washing position.

Bowl 30 may be moved between the open and closed positions by any means known in the art. Preferably, bowl 30 is pivotally mounted along a generally horizontal pivot axis by means of bearings 32. In this way, the bowl or sink 30 can be rotated to open outwardly for washing (FIG. 2 and FIG. 4) and rearwardly into a covered inactive position for rinsing and disinfecting (FIG. 3) by suitable motor and crank means 33. While the bowl is described as being rotatably mounted, other forms of moveable mounting are possible. Thus, the bowl could simply slide in and out. Preferably, bowl 30 is mounted so that, when it is in the hand washing position, it is mounted at a suitable height for a user to wash their hands.

It will be appreciated by those skilled in the art that bowl 30 may be of any particular shape and that the actual shape of bowl 30 may vary depending upon whether bowl 30 is movably mounted and, if so, how it moves. For example, if bowl 30 is pivotally mounted, then bowl 30 is preferably of a generally semi-spherical shape. Thus, when rotated rearwardly to the closed position (FIG. 3), the underside of 30a of the bowl presents a smooth generally convex appearance, effectively closing and sealing the interior of the entire apparatus and preventing contamination by garbage or debris or personal contamination. Alternately, if bowl 30 is slideably mounted so as to slide in and out, then bowl 30 may be cylindrical in cross section.

Located to one side of the bowl, within the interior enclosed by front wall 16, is a water outlet indicated generally as 34. Nozzle 34 is positioned to direct water, preferably at a median temperature suitable for hand washing, into bowl 30 for wetting of the hand. Water may be supplied to nozzle 34 by a pump (not shown), or simply by using the main's water pressure through a pressure regulator.

A cleaner, e.g. soap, is supplied for washing. The cleaner may be dispensed by passing the water through a suitable water/cleaner mixing valve 36 upstream from nozzle 34. Accordingly, valve 36 may be connected to a supply of cold water via conduit 36a and connected to a water heater 37 contained within the apparatus via conduit 36b, and controllable so as to supply a warm water mix at an appropriate temperature for washing hands. Pursuant to this embodiment, there is provided a container 38 for storing a cleaner for use when a user washes or rinses their hands. A plurality of such containers may be provided, each of which may contain a different cleaning compound. For example, as shown in FIG. 1, a soap container 38 and a disinfectant liquid material tank 39 are connected to the nozzle 34. The container or containers may thus supply a soap, disinfectant or the like to the valve 36 for mixing with the water preferably at an appropriate concentration of cleaner to water.

In alternate embodiment, if the cold water supply is at a suitable temperature, then hot water heater 37 will not be required. Instead, the cold water supply may be fed directly to mixing valve 36 without combining the cold water with any heated water. This approach may also be used if a hot water supply and a cold water supply are first connected to a mixing valve and the mixing valve is then connected to the inlet water port for housing 10 (not shown).

Alternately, the cleaner may be dispensed by a dispenser directly onto the hands of the user without the user using their hands to operate the dispenser. For example, the dispenser could be actuated by an optical sensor or by a remote actuator, eg. a foot pedal (not shown). According to this embodiment, the user may place their hands below the dispenser at which time the optical sensor will sense the presence of the user's hand thereunder and dispense an aliquot of cleaner or at which time the user may actuate the foot pedal. A plurality of dispensers, each with an associated actuator, may be provided.

If bowl 30 is rotatably mounted, it preferably has a rearwardly directed drain spout 40, for discharge of its contents, when it is rotated rearwardly. If bowl 30 is slideably or fixedly mounted, then spout 40 may be positioned at the lowest point of bowl 30 when bowl 30 is in use.

In order to catch the wash water, residue and any disinfectant from bowl 30, bowl 30 may be in turn preferably mounted over a sink 42, which is fixed within the interior of front wall 16, and is connected by a conventional plumbing waste pipe 44 to a sump 46. In this way, when bowl 30 is rotated rearwardly, it will dump all of its contents through spout 40 into sink 42 and down the waste pipe 44. It will be appreciated that if bowl 30 is not rotatably mounted, it may be directly connected to waste pipe 44.

The water mixer, soap container 38 and disinfectant container 39 and their pumps 38a, 39a may be connected through a suitable timing mechanism (e.g. controller 70) so as to provide a timed operation for washing, for example, an initially wetting of the hand, followed by a soaping of the hands, followed by a rinsing of the hands in warm rinse water. At the end of the cycle, the washer may be automatically reconfigured to the closed position, such as by bowl 30 rotating rearwardly. It will be appreciated that alternate washing cycles may be preprogrammed. The user may select a desired cycle before use by pushing a button or by tripping an optical sensor (not shown). The different cycles may employ different chemical mixtures and/or may use shorter or longer periods of washing and/or rinsing. For example, there may be a quick rinse cycle when a full wash is not required. It will also be appreciated that the wash cycle may be manually controlled. For example, by a series of foot pedals or a series of optical sensors.

After washing, the washing bowl 30 is then preferably cleaned by water such as cold water which is supplied to the mixing valve 36 by the mains, receiving cold water from the conventional cold water supply together with a disinfectant, for washing and cleaning the bowl. Hot water could be used if desired. The washing mixture will drain out of bowl 30 through spout 40 and into sink 42. The bowl may then be dried by air being drawn from outside.

In the preferred embodiment, the apparatus is operable without the user's hands contacting the apparatus once the washing cycle commences. For example, the operation of the washer could be actuated by a user pushing a start button or by a user inserting coins into a coin fed actuator as are know in the vending machine industry (not shown). More preferably, the entire cycle of the machine, including the reconfiguration of bowl 30 and its cover, is actuated without the user's hands touching any of the controls. For example, the entire operation of bowl 30 and the water and soap dispenser may be initiated by means of an actuator, such as a foot operated pedal 50 (FIG. 2) or an optical sensor or a proximity sensor keyed to a securing card (not shown) so that the user's hands do not touch any of the controls after the washing cycle commences.

In order to dry the user's hands, a hot air dryer nozzle 52 is preferably provided (FIG. 1). Hot air nozzle 52 may be provided to supply heated and, preferably, heated and disinfected air. For this purpose, an air disinfecting chamber 54 may be provided with, for example, ultraviolet light tube 55. Air may be drawn inwardly through nozzle 56 then through a suitable filter 57 and heater and fan 58 before exiting at the nozzle 52. Preferably, nozzle 56 may also be provided with filter 57a to prevent contaminants from entering, or reduce the contaminants entering, nozzle 56. By providing filter 57a for nozzle 56, the surface of filter 57a may be positioned so as to be exposed to the ultraviolet light emanating from ultraviolet light tube 55 thus helping to reduce the contamination of filter 57a. Nozzle 52 and a fan (not shown) are preferably timed (eg. by controller 70) to supply sufficient hot air for the drying of the hands after rinsing. The drying cycle may be controlled by an optical sensor as is known in the art. In this way, not only are the hands thoroughly cleaned and washed without contact with any part of apparatus, but they are also dried by disinfected air.

When bowl 30 rotates rearwardly, it may then be rinsed, disinfected and dried. To this end, the air which is drawn through nozzle 56 may first be drawn around bowl 30 rendering it dry and clean for the next user. If desired, this drying air could also be disinfected and/or heated. Alternately, air from hot air nozzle 52 may be used to dry bowl 30.

From time to time, it may be desirable for service personnel to wash down the entire unit. For this purpose, a flexible hose 60 may be provided. Flexible hose 60 preferably has a manually operable jet nozzle 62 and is connected to the water supply within the apparatus such as through a suitable valve 64 designed to be operable only by the service personnel so as to prevent vandalism and abuse.

As shown in FIG. 1, the device preferably includes a safety feature, namely optical sensor 66, which senses the presence of a person's hands in the vicinity of bowl 30 when it is open. This optical sensor prevents reverse rotation of bowl 30 so long as the person's hand are still in the vicinity of bowl 30, thereby preventing a possible injury. It may also include a light to illuminate the hands so that a person can check for cleanliness.

Figure 5:
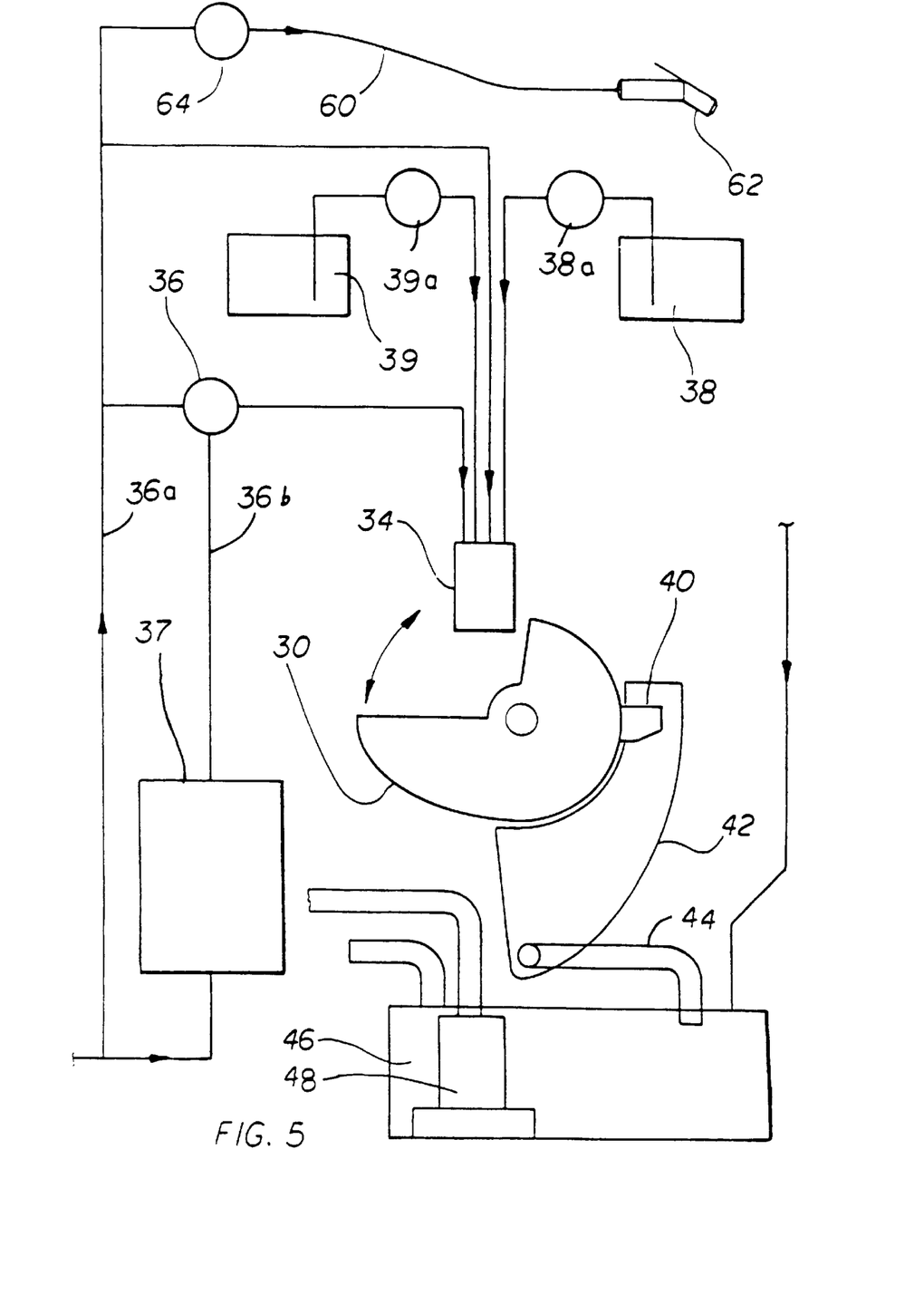
FIG. 5 is a plumbing diagram showing the water inflow and outflow routing.

It will, of course, be appreciated that there are a large number of detailed electrical connections and controls and valves and relays. Reference to the plumbing diagram FIG. 5 and block diagram FIG. 6 will clarify the operation of the apparatus, and be a sufficient explanation for persons skilled in the art to understand the design and construction of the apparatus.

Figure 6:
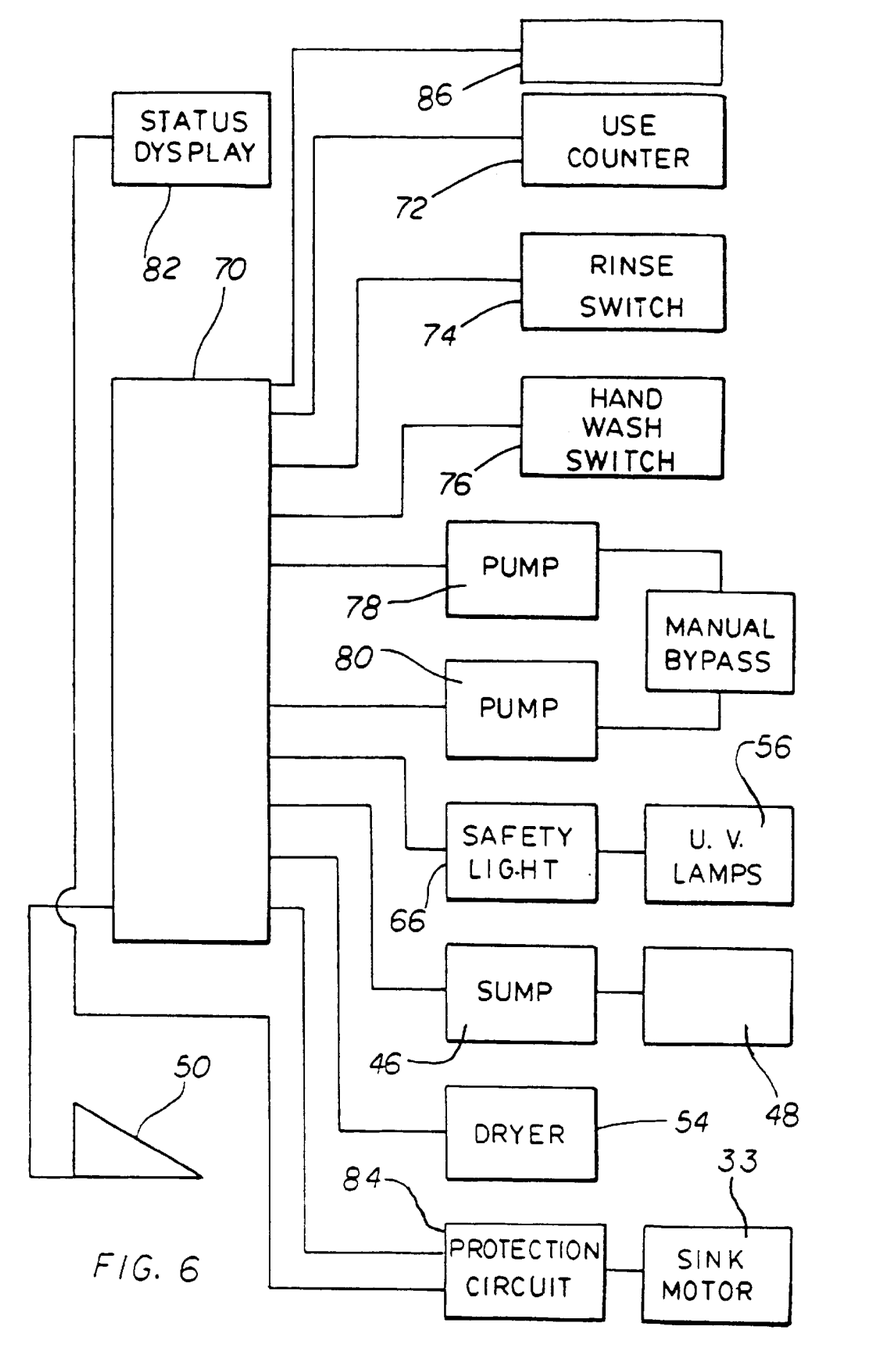
FIG. 6 is an electrical block diagram showing the basic controls, and their relation to a foot switch.

As shown in FIG. 6, a main controller 70, which may be operated by, e.g., foot switch 50, may be connected to a use counter 72, a rinse switch 74 and a hand wash solenoid 76. It may also be connected to two pumps 78 and 80 and to a bowl operation protection device 66 already referred to and the ultraviolet light tube 56, and to the dryer operation 54.

With the sump reservoir 46, a pump 48 is preferably provided to periodically empty the sump. The reservoir can also be connected to the main plumbing drainage if desired.

A status display 82 may be connected to the controller via the protection circuit 84, so as to provide a visible display of the operative status of the apparatus.

The operation of the whole apparatus is self-evident from the foregoing description. In the preferred embodiment of the Figures, in the storage position, bowl 30 is normally positioned rotated rearwardly so that the hemispherical underside of the bowl is directed outwardly, thereby rendering the entire apparatus secure, and sealed all around the bowl. A user wishing to use the apparatus will first of all operate the foot control, and a sequence of operations may then be started as follows:

A. Bowl 30 rotates to the open position.

B. Clean water at the controlled temperature is dispensed over the hands to wet the hands prior to the washing step.

C. A cleansing solution of water and soap or other disinfectant or cleaner is then mixed with the water and then dispensed over the hands so that the hands may be washed.

D. A rinsing solution of water at the controlled temperature is then dispensed over the hands so that the hand may be rinsed clean.

E. The hands are then withdrawn from the bowl and bowl 30 rotates closed, dumping the washing water into the sink 42, where it flows under gravity to the sump tank. Prior to the withdrawal of the hands from bowl 30, the bowl is prevented from closing inadvertently by the safety light.

F. A hot-air jet is then directed over the hands, having been first of all passed through the ultraviolet chamber to disinfect the air.

G. Water and a disinfectant mixture is then sprayed around the interior of the bowl, while it is closed, to disinfect the interior of the bowl. Air is drawn in around the bowl to dry it. This may be the air drawn in to feed the hot-air jet. In some cases, this air may be first disinfected and heated.

If desired, air, either hot or cold, can be directed around the side areas of the front panel on the side of the bowl, the sink and also around the floor next to the foot pedal to dry any moisture that may have escaped.

The counter 72 will record usage. In a more preferred embodiment, the device may also include a sensor 86 so as to identify the actual user. Thus counter 72 may identify the actual user, the actual wash cycles activated by the user and the time when the user used the washer. Sensor 86 may be any type which is known in the art. For example, sensor 86 may be adapted to identify a user by the security badge which the user might otherwise carry. For example, sensor 86 may be adapted to read a magnetic strip. Thus, in order to be able to activate the unit, the user must first swipe their card through sensor 86 and then proceed as described above. Alternately, sensor 86 may be of the proximity sensor type so that by placing the security badge near sensor 86, it will identify the user, or it may include a bar code reader to read a bar code affixed, for example, to a security badge.

After an appropriate count of uses, maintenance personnel may then check the apparatus, clean it and wash it down, and refill the various containers.

The apparatus will be seen to provide both an effective disinfected means of cleaning the hands, without the user's hands contacting any contaminants once the washing cycle commences as the cleaning water is operated automatically without manual control, the soap dispenser is operated automatically without manual control and the bowl itself may be cleansed and disinfected between each usage after which the user's hands may be dried by disinfected hot air. The whole operation as far as the user is concerned may be controlled by means of a foot pedal or the like thereby removing further sources of contamination common to conventional hand cleaning facilities.

The controlling of a washing cycle is designed to meet the various codes, such as FDA requirements. The invention preferably controls the sequence of event, the timing and duration, temperatures, the solution mixes, the cleaning of the bowl, the drying of the hands, as well as recording the successful completion of this sequence.

The foregoing is a description of a preferred embodiment of the invention which is given here by way of example only. The invention is not the be taken as limited to any of the specific features as described, but comprehends all such variations thereof as come within the scope of the appended claims.

I claim:

1. A method for a person to wash their hands using a hand washing apparatus comprising a hand washing bowl having an interior and a cover which are reconfigurable between a hand washing position in which the person can wash their hands and an inactive position, a controller for reconfigurating the bowl between the hand washing position and the inactive position; and, a dispenser for dispensing water and a cleaner over the person's hands, the method comprising the steps of:

(a) actuating the controller to rotate the bowl and the cover about an axis to the hand washing position;

(b) dispensing water and soap over the person's hands; and, (c) dispensing water to rinse the person's hands.

2. The method as claimed in claim 1 further including dispensing a stream of hot air over the hands of the person.

3. The method as claimed in claim 1 further including dispensing a disinfectant into the bowl when the bowl is in its inactive position, for flowing around the interior of the bowl and rendering the same clean.

4. The method as claimed in claim 3 further including dispensing an air stream to dry the bowl after the bowl has been cleaned.

5. The method as claimed in claim 1 wherein the apparatus also has a controller that is preprogrammed with at least two different washing cycles and the method further includes selecting a washing cycle whereupon various fluids are thereafter automatically dispensed.

6. The method as claimed in claim 1 wherein the apparatus also has a sensor for recognizing a particular person and the method further comprises using a card to identify the person to the apparatus prior to a washing cycle being activated.

7. The method as claimed in claim 6 wherein the person presents an identity card to a sensor to activate the apparatus.

8. The method as claimed in claim 1 further comprising moving the hand washing bowl to the inactive position after the person has washed their hands.

9. A method for a person to wash their hands using a hand washing apparatus comprising a hand washing bowl which is reconfigurable between a hand washing position in which the person can wash their hands and an inactive position said method comprising the steps of:

(a) rotating the bowl to place the hand washing bowl in the hand washing position;

(b) dispensing a solution for use by the person in washing their hands; and, (c) dispensing water to rinse the person's hands.

10. The method as claimed in claim 9 further including the step of moving the hand washing bowl to the inactive position after the person has washed their hands.

11. The method as claimed in claim 10 wherein the bowl is automatically moved to the inactive position after the person has washed their hands.

12. The method as claimed in claim 9 further including the step of dispensing a stream of hot air over the hands of the person.

13. The method as claimed in claim 9 further including the step of disinfecting the bowl when the bowl is in its inactive position.

14. The method as claimed in claim 13 further including the step of drying the bowl after the bowl has been cleaned.

15. The method as claimed in claim 14 further comprising the step of presenting an identity card to a sensor to activate the apparatus.

16. The method as claimed in claim 9 wherein the apparatus also has a controller that is preprogrammed with at least two different washing cycles and the method further includes the step of selecting a washing cycle whereupon various fluids are thereafter automatically dispensed.

17. The method as claimed in claim 9 wherein the apparatus also has a sensor for recognizing a particular person and the method further comprises the step of using a card to identify the person to the apparatus prior to a washing cycle being activated.

* * * * *